US012558447B2

(12) United States Patent
Högerle et al.

(10) Patent No.: US 12,558,447 B2
(45) Date of Patent: Feb. 24, 2026

(54) SMART OIL SPRAY ADAPTER

(71) Applicant: Aesculap AG, Tuttlingen (DE)

(72) Inventors: Roland-Alois Högerle, Tuttlingen (DE); Uwe Schaz, Neuhausen (DE)

(73) Assignee: AESCULAP AG (DE)

( * ) Notice: Subject to any disclaimer, the term of this patent is extended or adjusted under 35 U.S.C. 154(b) by 532 days.

(21) Appl. No.: 17/920,278

(22) PCT Filed: Apr. 15, 2021

(86) PCT No.: PCT/EP2021/059746
§ 371 (c)(1),
(2) Date: Oct. 20, 2022

(87) PCT Pub. No.: WO2021/213876
PCT Pub. Date: Oct. 28, 2021

(65) Prior Publication Data
US 2023/0201398 A1     Jun. 29, 2023

(30) Foreign Application Priority Data

Apr. 22, 2020    (DE) .......................... 102020110867.2

(51) Int. Cl.
*A61L 2/00*        (2006.01)
*A61B 90/70*        (2016.01)
(Continued)

(52) U.S. Cl.
CPC ................ *A61L 2/26* (2013.01); *A61B 90/70* (2016.02); *A61B 90/98* (2016.02); *A61L 2/22* (2013.01);
(Continued)

(58) Field of Classification Search
CPC ......... C23F 11/04; B05B 12/00; A61M 15/00; A61M 15/0065
(Continued)

(56) References Cited

U.S. PATENT DOCUMENTS 4,486,174 A * 12/1984 Eibofner ............... B05B 12/081
                                                       433/104
4,736,871 A     4/1988 Luciani et al.
(Continued)

FOREIGN PATENT DOCUMENTS

CN        104549829 A       4/2015
CN        109561673 A       4/2019
(Continued)

OTHER PUBLICATIONS

German Search Report for German Application No. 10 2020 110 667.2, with partial translation, dated Dec. 14, 2020, 11 pages.
(Continued)

*Primary Examiner* — Monzer R Chorbaji
(74) *Attorney, Agent, or Firm* — Buchanan Ingersoll & Rooney PC

(57)        ABSTRACT

Provided is an adapter for connection to a spray can dispensing an oil-containing aerosol. The adapter comprises a timepiece configured to measure a predetermined time interval, the starting point of the time measurement being defined by the start of a spraying process of the spray can; and an indicating element configured to indicate to the user, once the predetermined time interval has expired, to end the spraying process. Also provided is a method for manually reprocessing a medical device.

17 Claims, 3 Drawing Sheets

(51) Int. Cl.

| | |
|---|---|
| *A61B 90/98* | (2016.01) |
| *A61C 1/02* | (2006.01) |
| *A61L 2/08* | (2006.01) |
| *A61L 2/22* | (2006.01) |
| *A61L 2/24* | (2006.01) |
| *A61L 2/26* | (2006.01) |
| *A61M 11/00* | (2006.01) |
| *B65D 83/26* | (2006.01) |
| *B65D 83/285* | (2025.01) |
| *B67D 5/38* | (2006.01) |

(52) U.S. Cl.
CPC .............. *A61L 2/24* (2013.01); *B65D 83/26* (2013.01); *B65D 83/285* (2013.01); *A61L 2202/11* (2013.01); *A61L 2202/14* (2013.01); *A61L 2202/15* (2013.01); *A61L 2202/24* (2013.01)

(58) Field of Classification Search
USPC ........... 433/104; 422/27, 50, 119, 292, 300; 128/200.14; 239/74
See application file for complete search history.

(56) References Cited

U.S. PATENT DOCUMENTS

| | | | | |
|---|---|---|---|---|
| 6,068,815 | A | * | 5/2000 | Oberleitner ............. C23F 11/04 |
| | | | | 134/22.12 |
| 6,119,684 | A | | 9/2000 | Nohl et al. |
| 6,247,871 | B1 | | 6/2001 | Nickel |
| 9,782,551 | B2 | * | 10/2017 | Morrison .......... A61M 15/0065 |
| 2004/0209223 | A1 | | 10/2004 | Beier et al. |
| 2008/0017664 | A1 | | 1/2008 | Haste et al. |
| 2012/0048883 | A1 | | 3/2012 | Heckenberger et al. |
| 2012/0298151 | A1 | | 11/2012 | Heckenberger et al. |
| 2013/0269685 | A1 | * | 10/2013 | Wachtel ............ A61M 15/0065 |
| | | | | 128/200.14 |
| 2014/0084075 | A1 | * | 3/2014 | Vandelli ................... G01F 1/34 |
| | | | | 239/74 |
| 2014/0130602 | A1 | | 5/2014 | Heckenberger et al. |

| | | | |
|---|---|---|---|
| 2016/0325057 | A1 | 11/2016 | Morrison et al. |
| 2019/0000065 | A1 | 1/2019 | Gutsmann |
| 2019/0175302 | A1 | 6/2019 | Gotani et al. |
| 2019/0366020 | A1 | 12/2019 | Tritschler et al. |
| 2022/0232815 | A1 | 7/2022 | Gutsmann et al. |

FOREIGN PATENT DOCUMENTS

| | | | |
|---|---|---|---|
| DE | 3104237 | A1 | 8/1982 |
| DE | 4422710 | C1 | 9/1995 |
| DE | 102010002028 | A1 | 10/2010 |
| DE | 102009051620 | A1 | 5/2011 |
| DE | 212011100070 | U1 | 12/2012 |
| DE | 102015004073 | B3 | 7/2016 |
| EP | 3299036 | A1 | 3/2018 |
| EP | 3584545 | A1 | 12/2019 |
| JP | 2011139911 | A | 7/2011 |
| JP | 2013519477 | C2 | 5/2013 |
| JP | 2017202145 | A | 11/2017 |
| WO | 9312823 | A2 | 7/1993 |
| WO | 2011157561 | A1 | 12/2011 |
| WO | 2020239664 | A1 | 12/2020 |

OTHER PUBLICATIONS

International Search Report and Written Opinion for International Application No. PCT/EP2021/059746, dated Sep. 6, 2021, 8 pages.
English Translation of the Written Opinion for International Application No. PCT/EP2021/059746, dated Sep. 6, 2021, 6 pages.
Office Action (Notice of Reasons for Rejection) issued Mar. 24, 2025, by the Japanese Patent Office in corresponding Japanese Patent Application No. 2022-564020 and an English translation of the Office Action. (13 pages).
Office Action (Communication pursuant to Article 94(3) (EPC) issued Nov. 4, 2025, by the European Patent Office in corresponding European Patent Application No. 21 719 595.7 and an English machine translation of the Office Action. (9 pages).
Office Action (The First Office Action) issued Dec. 5, 2025, by the State Intellectual Property Office of People's Republic of China in corresponding Chinese Patent Application No. 202180019950.7 and an English machine translation of the Office Action. (16 pages).

* cited by examiner

SMART OIL SPRAY ADAPTER

This application is a U.S. National Phase application of PCT International Application No. PCT/EP2021/059746, filed Apr. 15, 2021, which claims the benefit of DE 102020110867.2, filed Apr. 22, 2020, both of which are incorporated by reference herein.

The invention relates to an adapter for connection to a spray can dispensing an oil-containing aerosol and to a method for manual reprocessing of a medical device.

PRIOR ART

In medical technology, various reprocessing procedures are provided for different products, commonly referred to herein as medical devices. Medical products contaminated with pathogens (e.g. electromotive instruments) can be the source of infections in humans. The use of such medical products therefore requires prior reprocessing, for which defined requirements must be met. Reprocessing of medical products intended for low-germ or sterile use can be understood as the cleaning, disinfection and sterilization carried out after the initial use for the purpose of renewed use, including the associated work steps as well as the testing and restoration of the technical and functional safety. In the following, reprocessing is primarily understood to mean the restoration of technical and functional safety.

The prior art offers both machine-related reprocessing and manual reprocessing. For example, for machine-related reprocessing, maintenance stations for dental handpieces are used which automatically clean and oil mechanical components such as gears, bearings, actuating mechanisms, etc. arranged inside an instrument housing. For the manual maintenance of medical devices, such as dental and surgical handpieces and motor systems, oil sprays, i.e. oil in spray cans/aerosol cans, are used to spray the medical device or its mechanical elements. This is sometimes provided or pre-scribed by the manufacturers themselves.

The oil lubricates and maintains the mechanical elements, for example mechanical components such as gears and bearing points (in particular roller and friction bearings). The manufacturer can specify how long the spraying process should/must take, for example 2 seconds. The optimum duration of the oiling depends on the respective motor/handpiece of the corresponding medical device.

However, the prior art has the disadvantage that user errors are almost inevitable when using spray cans for manual reprocessing/maintenance of medical products. Specifically, three major application errors can occur:

1) The prescribed period is not kept. As a result, insuffi-cient lubrication or over-oiling of the mechanical ele-ments may occur.

2) The spray can is not held (exactly) vertically. As a result, the rising pipe generally located in the spray can may partially suck in propellant gas (in particular when the can level is low), which is sprayed out unnoticed instead of lubricating oil. This can result in insufficient lubrication.

3) A residual oil quantity in the spray can that is still available for the upcoming reprocessing/maintenance process is not sufficient. This inevitably results in insufficient lubrication.

In order to avoid these problems as far as possible, a user usually takes the safest route of prematurely disposing of a spray can whose residual oil supply would still have been sufficient for the upcoming reprocessing/maintenance pro-cess, and tends to exceed the prescribed time for the spraying process. However, this in turn leads to the problem of excessive material consumption. Thus, there may be a need to provide concepts for devices/reprocessing/maintenance systems and methods to prevent or reduce user errors, in particular of the type described above.

BRIEF DESCRIPTION OF THE INVENTION

Thus, it is the object of the invention to avoid or at least reduce the disadvantages of the prior art. In particular, various user errors in the reprocessing/maintenance of medi-cal devices are to be avoided in order to ensure the technical/functional safety of the medical devices.

This object is solved in a generic reprocessing/mainte-nance device or a generic reprocessing/maintenance system according to the invention by providing an (intermediate) adapter. The adapter is provided to be connected to a spray can, preferably a spray can dispensing an oil-containing aerosol, and thus to virtually form an intermediate piece for (fluidic) coupling of the spray can and the medical product to be reprocessed/maintained (handpiece). According to the invention, the adapter is equipped with smart functions that record the application parameters and preferably also the state parameters of the spray can and inform the user accordingly.

For example, the adapter has/includes a timekeeper. The timekeeper is configured to perform a time measurement for a predetermined time interval. The starting point of the time measurement is indicated by a start of a spraying process of the spray can. Furthermore, the adapter comprises/has, for example, an indicating element. The indicating element is configured, upon completion of the predetermined time interval, to indicate to the user to terminate the spraying process. The indicating element may be of visual and/or acoustic design.

This has the advantage that the user of the spray can is able to determine whether, on the one hand, not too much and, on the other hand, not too little oil-containing aerosol has been supplied to the medical device. This ensures the technical and functional safety of the medical devices.

The adapter may be a mechanical adapter for connecting to the dispensing opening of the spray can. The adapter may also be understood as a plug-in or screw connector for the mechanical connection of the spray can to the medical device.

The spray can may also be referred to as a spraying can or aerosol can and is, for example, a metal can for spraying the oil-containing aerosol or an oil-containing liquid, respec-tively. Here, preferably only oil is used as the liquid.

The timekeeper may also be understood as a timer, which may act herein as a control module to communicate a signal to the indicating element about the end of the time interval. The timer may be implemented as software in a processing unit of the adapter or as hardware (for example, an electronic circuit).

The predetermined time interval may be or may be intended to be adapted to the medical device. For example, the predetermined time interval may have a duration of less than 5 seconds, in particular less than 4 seconds, or less than 3 seconds, or less than 2 seconds. For example, the time interval may be 1.5 seconds or 3 seconds. For this purpose, the adapter may also be provided with an input unit, if necessary, to set the timekeeper accordingly.

The starting point may be in connection with the actuation of the spray can. For example, the adapter can interact with the spray can in such a way that by actuating the spray can itself (actuating an actuating lever on the spray can), the timekeeper starts or respectively performs the time measurement. Alternatively, a flow inside the adapter or a temperature change caused by the flow can be detected (adapter-autonomous spray start detection), from which the start of a reprocessing/maintenance process can be detected.

The indicating element may, for example, be a visual indication, such as an LED, and/or an acoustic indication, such as a loudspeaker or beeper. This can be used to indicate to the user whether the predetermined time interval is completed. After the time interval is completed, the user can stop actuating the spray can accordingly and can detach/remove the adapter from the spray can and/or the medical device.

The spraying process is generally referred to herein as the process for dispensing the liquid contained in the spray can.

Advantageous embodiments are claimed in the dependent claims and are explained in more detail below.

A first advantageous further development of the reprocessing and/or maintenance system is that the adapter can have sensor system that is set up to establish a smart connection, in particular via NFC or BLE radio technology, with a medical device to be connected, in particular a smart tray or a medical instrument.

In another advantageous further embodiment, the sensor system of the adapter can be set up to identify the type of medical device by means of the smart connection and to recognize whether it is connected directly or indirectly to the adapter.

In another preferred embodiment, the sensor system of the adapter may be arranged to exchange, process and store data between the adapter and the medical device by means of the smart connection, and wherein the data of the medical device is preferably stored on an RFID chip.

The adapter may further comprise/include a first port. The first port may be provided and configured to be connected to the spray can. In operation, the first port may be connected to the spray can. The adapter may further comprise a second port. The second port may be provided and configured to be connected to a (particular) medical device. In operation, the second port may be connected to the medical device. The adapter may further include/comprise a passage. The passage may be provided and configured to connect the first port to the second port. Furthermore, the passage may be provided to guide or respectively transport an aerosol dispensed by the spray can therein from the first port to the second port.

Thus, a continuous passage connection between spray can and medical device can be provided via the first and second port.

In particular, both connections may be plug-in connections. A connection can be provided here by force fit or form fit. Advantageously, plug connectors can be used as ports. The connection of the ports may also be provided in the form of a screw connection. The first and second connections may in particular provide detachable connections with the spray can or the medical device, respectively.

The adapter may further include/comprise a temperature sensor. The temperature sensor may be configured to detect a temperature drop in the passage. The timekeeper may be configured to determine the start of the spraying process based on the temperature drop in the passage. The temperature sensor may be in the form of an electrical or electronic device that provides an electrical signal as a measure of temperature. Hot conductors (NTC) and/or cold conductors (PTC) can be used for this purpose. Temperature sensors or integrated semiconductor temperature sensors such as solid-state circuits can also be used for this purpose.

The temperature drop can thus be used to infer the aerosol flow through the passage. This allows the predetermined time interval for using the spray can to be set relatively accurately without pressing a key. When the temperature drop is detected, the time measurement (for the predetermined time interval) can be started.

The temperature drop may be triggered by the aerosol that is transported colder than an ambient air located in the passage. In particular, a temperature drop can occur when the aerosol is sprayed due to the relaxation cold. Thus, the signal from the temperature sensor can be used to start the timer for the time measurement/indication (buzzer/LED). At this point, it should already be pointed out that in particular the temperature measurement can also be used to determine whether a liquid (lubricating oil) or a gas (propellant gas) is currently being dispensed from the spray can, provided that corresponding characteristic temperature curves/drops are known and these can be compared with the measured temperature curves for comparison.

In another advantageous embodiment, the adapter may include/comprise a pressure sensor. The pressure sensor may be configured to detect a pressure change in the passage. The timekeeper may further be configured to determine the start of the spraying process based on the pressure change in the passage.

In particular, absolute pressure sensors, differential pressure sensors, bidirectional differential pressure sensors, relative pressure sensors, and/or barometric pressure sensors may be used as pressure sensors, for example, to detect the pressure change in the form of an air pressure present in the passage. A change in pressure may occur during start of spraying. Thus, the signal from the pressure sensor can be used to start the timer for the time measurement/indication (buzzer/LED) or to detect whether the can is empty.

Thus, when the pressure change is detected, the time measurement (for the predetermined time interval) can be started.

Furthermore, the adapter may further include/comprise a humidity sensor. The humidity sensor may be configured to detect an oil proportion of the oil-containing aerosol in the passage. The indicating element may be configured to indicate to the user to terminate the spraying process based on the oil proportion. The humidity sensor may be a capacitive sensor for measuring humidity in the passage. Here, an electrical capacitance may be measured, which depends on the dielectric constant, which depends on the oil content in the passage. During the spraying process, the aerosol or oil mixture can wet the humidity sensor. This enables the humidity sensor to detect whether oil is still present or only propellant gas is flowing out, e.g. because the can is empty or the bottle is held with too much of an inclination.

Likewise, the adapter may further include/comprise a position sensor. The position sensor may be configured to determine an orientation of the spray can. The indicating element may be configured, based on the orientation of the spray can, to indicate to the user to terminate the spraying process if/when the spray can orientation becomes an unacceptable value. Orientation may be understood herein to mean how the spray can is inclined relative to the earth's gravity. If the inclination of the spray can relative to a normal to the earth's surface exceeds a threshold value, for example 20 degrees or 30 degrees, then the position sensor may indicate to the indicating element that the spraying process should be terminated.

In a further embodiment, the adapter may further include/comprise a power supply. The power supply may be configured to supply power to the components of the adapter.

The power supply may be a battery or an accumulator. In particular, the power supply may power the timekeeper, the position sensor, the temperature sensor, the humidity sensor, and/or the pressure sensor.

This allows the adapter to be configured to be small and modular.

The object defined above is solved in a further generic method according to the invention by providing a method for manual reprocessing of a medical device. The method comprises the following steps:

Providing a medical device.

Providing a spray can.

Providing an adapter in particular the adapter according to the invention with smart functions.

Connecting a first port of the adapter to the spray can.

Connecting a second port of the adapter to the medical device.

Carrying out a spraying process of the spray can for supplying mechanical components of the medical device with a reprocessing and/or maintenance agent, preferably an oil-containing aerosol, by manual actuation of the spray can by an operator/user.

Starting a time measurement by at least one smart function for a predetermined time interval, wherein the starting point is detected by detecting the manual start of the spraying process of the spray can.

Indicating the completion of the predetermined time interval for a manual termination of the spraying process.

These steps may be performed either in this order or in a different order.

In other words, the invention relates to a reprocessing/maintenance system comprising a maintenance-agent spray can (oil spray can) and an oil spray adapter that is intelligent/equipped with smart functions for (fluidic) coupling of the spray can with a medical instrument to be reprocessed/maintained as well as an adapter for such a system. In particular, the three significant user errors already listed above can be avoided when using oil sprays.

In one example, a time duration can be kept in the present case. When using a reprocessing unit for medical products ('RUMP'), these are usually measured according to one's own sense of time and not with a stopwatch. Due to this subjective feeling of time, the real time durations can vary from too short to far too long. This may result in insufficient lubrication or even over-oiling of the product. Insufficient lubrication can lead to wear, noise, gear or bearing damage and premature failure. Over-oiling can lead to heat development in high-speed drives and/or leakage of the excess oil during use, possibly in-situ.

In the same or another example, a vertical position can be maintained. Most spray systems can be constructed in such a way that a rising pipe leads from the spray head to the bottom of the can. If the can is held vertically, the rising pipe can always be surrounded by the oil and the oil dispensing is optimal. If the can is held improperly at an angle, a condition can occur such that the rising pipe is no longer in the oil supply, for example, and only propellant gas escapes. This application error can be strongly dependent on the fill level of the can. The lower the level is, the more serious is even minor slanting for causing this condition.

In the same or another example, it is possible to detect that a can is empty. A detection of the empty state of the can is for example only possible by shaking or test spraying on, for example, a piece of paper. Also, a lack of oil while only propellant is still coming out can still suggest to the user a correct application, although this is no longer the case.

One or more aspects may provide an application aid for independent and stand-alone use of oil spray cans.

According to one or more configuration examples, an avoidance of one or more of the most consequential sources of error in the use of oil spray cans is/are eliminated, for example:

incorrect spraying time by a visual and/or acoustic aid for adherence to the exact spraying time ideally matched to the respective handpiece/motor system, for example, to an accuracy of tenths of a second;

incorrect position of the can by visual and/or acoustic indication when the can is held at too great an angle; and failure to detect an empty state of the can by visual and/or acoustic indication when empty.

In an alternative, an intelligent oil-spray adapter can be provided as an attachment to a spray can or in a stationary manner, battery operated or accumulator operated. A time period may be fixed, individually adjustable or provided, for example, automatically by individual coded adapter attachments attachable to adapters and/or visual and/or acoustic signals.

In a further alternative, a timed indication for the spraying process may be provided. Here, for example, an LED can light up as an indicating element from the start and go out when the time period is over or the LED only lights up when the time period is over. Likewise, a signal tone (loudspeaker or buzzer as indicating element) can sound from the start and fall silent when the time period is over or the signal tone sounds only when the time period is over. The combination of the corresponding indicating elements visually and acoustically in the sense of LED/signal tone may also be provided.

According to one embodiment, a spraying process may be provided, for example, with a stop mechanism. In one example, an LED and/or (fast) signal tone may indicate when the spray can is held at an angle. In one example, an LED and/or signal tone may indicate when the spray can is empty. In one example, an LED and/or signal tone may indicate when the battery or rechargeable battery is empty.

Possible realizations of the sensors may be integrated in the adapter in the form of microchips. The sensors in microchip technology may be, inter alia, the temperature sensor, the humidity sensor, the position sensor, the pressure sensor, or an actuation sensor. The actuation sensor may interact with the push button of the spray can to establish the actuation of the push button as the start of the spraying process. When the spray head is pressed, the time measurement can thus be started. There may be complementary alternatives, for example in the sense of sensor fusion. An example would be the sole or joint use of pressure sensor, humidity sensor, and temperature sensor. The time measurement may be done by a timer or based on a temperature drop during the spraying process. For example, 10K may correspond to 1 s, 15K to 2 s, 25K to 3 s. An end of the time measurement can thus be defined by a maximum temperature threshold.

In particular, it may be provided that a visual and/or acoustic indication of the spray duration and/or a visual and/or acoustic warning is output if the spray can is positioned too obliquely. If the spray can is tilted, the position sensor can detect it, and if the spray can is empty, the moisture sensor can detect the oil moisture in the jet.

It is clear to the person skilled in the art that the explanations set forth herein may be/are configured to be implemented using hardware circuits, software means, or a combination thereof. The software means may be related to programmed microprocessors or a general computer, an ASIC (Application Specific Integrated Circuit) and/or DSPs (Digital Signal Processors).

For example, the adapter, the power supply, the temperature sensor, the humidity sensor, the position sensor, the pressure sensor, the actuation sensor, the indicating element, and the timekeeper may be partially implemented as a computer, a logic circuit, an FPGA (Field Programmable Gate Array), a processor (for example comprising a microprocessor, a microcontroller ($\mu$C) or a vector processor)/core (may be integrated in the processor or used by the processor)/CPU (Central Processing Unit; wherein multiple processor cores are possible), an FPU (Floating Point Unit), an NPU (Numeric Processing Unit), an ALU (Arithmetic Logical Unit), a co-processor (additional microprocessor to support a main processor (CPU)), a GPGPU (General Purpose Computation on Graphics Processing Unit), a parallel computer (for simultaneous execution of computing operations, inter alia, on multiple main processors and/or graphics processors), or a DSP.

Although some of the aspects described above have been described with respect to the adapter, these aspects may also apply to the method or a system comprising the adapter, spray can, and medical device. Likewise, the aspects described above with respect to the method may apply, in a corresponding manner, to the adapter and the system.

If it is said that a component is 'connected' or 'in connection' with another component, this can mean that it is directly connected with it; however, it should be noted that a further component may lie in between. If, on the other hand, it is said that a component is 'directly connected' to another component, this is to be understood to mean that there are no other components in between.

BRIEF DESCRIPTION OF THE FIGURES

The invention is explained below with the aid of drawings. The following is shown.

The figures are of a schematic nature only and are intended solely for the purpose of understanding the invention. Identical elements are provided with the same reference signs. The features of the individual embodiments can be interchanged.

In addition, spatially relative terms, such as 'located below', 'below', 'lower', 'located above', 'upper', 'left', 'on the left', 'right', 'on the right', and the like, may be used herein to simply describe the relationship of an element or structure to one or more other elements or structures shown in the figures. The spatially relative terms are intended to include other orientations of the component in use or in operation in addition to the orientation shown in the figures. The component may be oriented differently (rotated by 90 degrees or in a different orientation), and the spatially relative descriptors used herein may likewise be interpreted accordingly.

Figure Description

The adapter and the method, or respectively the system consisting of adapter, spray can, and medical device, are now described with reference to embodiments.

In principle, the disclosure herein relates to an adapter 30 for a spray can 20 that is provided to lubricate a medical device 40 or its elements, respectively. The adapter 30 serves to communicate any errors made by the user in manually operating the spray can 20 to the user themselves, thereby protecting the medical device 40 from damage or ensuring optimal performance of the medical device 40. For this purpose, time, inclination and oil content are taken into account in order to provide an optimal reprocessing of the medical device 40. In detail, reference is now made to all elements of the system.

Figure 1:
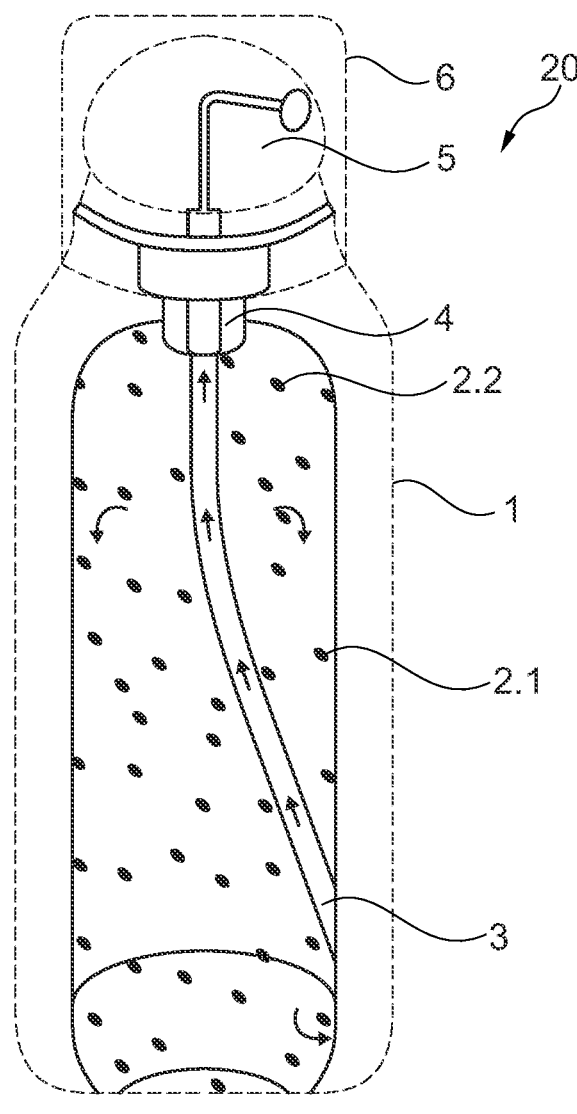
FIG. 1 shows a schematic representation of a spray can.

FIG. 1 shows a schematic representation of a spray can 20. The spray can 20 has a metal container 1, which is separated from an inner space. The inner space comprises, on the one hand, an active agent solution with propellant 2.1 in a liquid state and shown here by way of example at the bottom, since it is arranged substantially in the lower part of the spray can 20 when the bottle is held vertically. Above this, the propellant 2.2 is shown in a gaseous state, which is arranged substantially in the upper part of the spray can 20 when the bottle is held vertically. Within the space runs a rising pipe 3 for receiving the active agent solution. As shown in FIG. 1, this takes in the active agent solution 2.1 precisely when the lowest part of the rising pipe 3 is inside the active agent solution 2.1 in the space. If the spray can 20 is tilted and/or only a small amount of active agent solution 2.1 is left in the chamber, a larger amount of propellant 2.2 can enter the rising pipe 3. This is disadvantageous if this case remains unnoticed.

The rising pipe 3 leads to a valve 4, which prevents the active agent solution 2.1 and/or the propellant 2.2 from leaving the bottle. The valve 4 is opened by pressing/actuating the spray head 5 so that the active agent solution 2.1 and/or the propellant 2.2 can escape from the spray can 20. For the sake of completeness or as an example, FIG. 1 also shows the protection cap 6 of the spray can 20.

Further details and aspects are mentioned in connection with the embodiments described above or below. The embodiment shown in FIG. 1 may have one or more optional additional features corresponding to one or more aspects mentioned in connection with the proposed concept or embodiments described below with respect to FIGS. 2, 3a and 3b.

Figure 2:
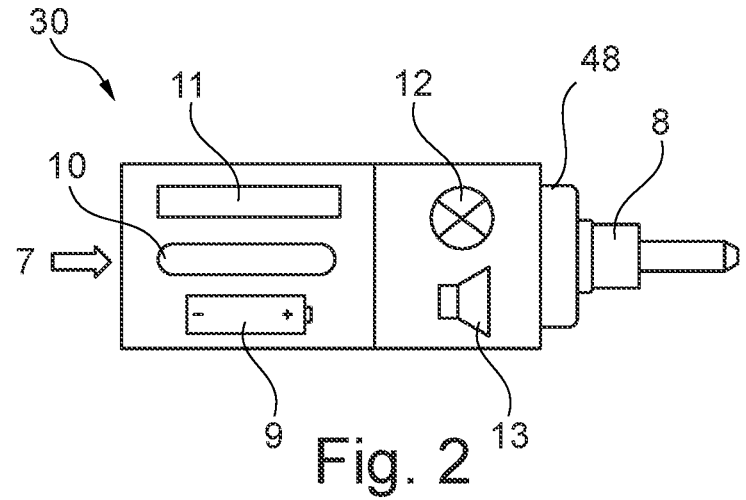
FIG. 2 shows a schematic representation of an adapter.

FIG. 2 shows a schematic representation of an adapter 30. The adapter 30 can in particular be provided for a spray can 20 as shown in FIG. 1. For this purpose, the adapter 30 has a first port 7 which can be connected to the spray can 20, for example by screwing or plugging it on, depending on which type of port is used for the first port 7. A passage (not shown) leads through the adapter 30 to a second port 8, which in turn can be connected to a medical device 40. The connection can advantageously be made by plugging. In FIG. 2, a power supply 9 in the form of a battery, a sensor 10 in the form of a position sensor, and a timekeeper 11 in the form of a timer are shown as examples. Specifically, the timekeeper can define a time interval beginning when the spray head 5 of the spray can is actuated. At the end of the time interval, either a visual indication 12 in the form of an LED or an acoustic indication 13 in the form of a beeper or buzzer may light up or sound, respectively, or both together. This tells the user to stop operating the spray can 20.

The battery 9 supplies the necessary energy or respectively the corresponding current for the corresponding energy consumers 10, 11, 12, 13 of the adapter 30. Cables may be routed for this purpose within a space provided by the adapter 30 and connect the energy consumers 10, 11, 12, 13 to the battery 9. A 3V or 5V voltage supply may be provided for this purpose. The energy consumers used may be integrated in the adapter in the form of microchips.

The position sensor 10 measures whether the adapter deviates from the horizontal plane in relation to the figure and transmits a signal to the visual indication 12 and/or to the acoustic indication 13 if the inclination to the horizontal in FIG. 2 exceeds a threshold value. The threshold value may be conservatively selected if the bottle is no longer completely full.

Further details and aspects are mentioned in connection with the embodiments described above or below. The embodiment shown in FIG. 2 may include one or more optional additional features corresponding to one or more aspects mentioned in connection with the proposed concept or one or more embodiments described above (e.g., FIG. 1) or below (e.g., FIGS. 3a, 3b, and 3c).

Figure 3A:
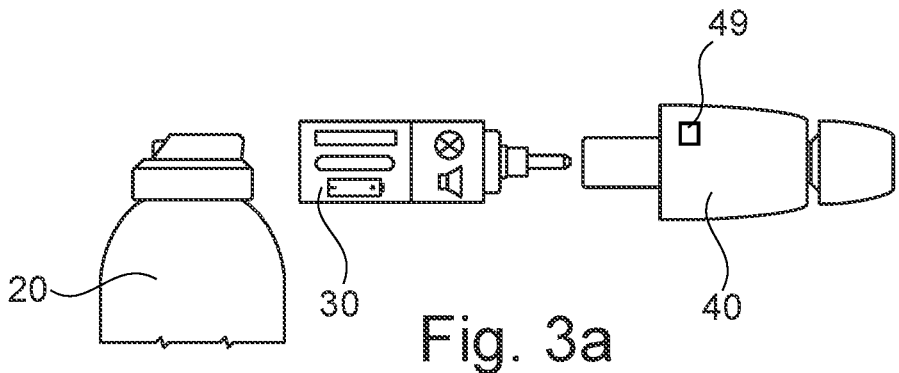
FIG. 3a shows a schematic representation of a system of spray can, adapter, and a first medical device.
Figure 3B:
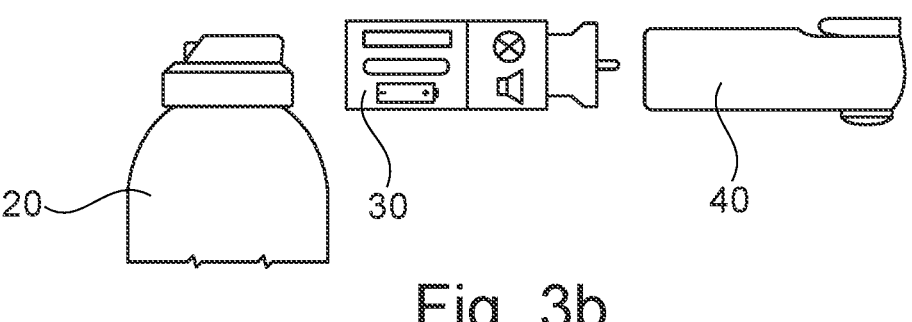
FIG. 3b shows a schematic representation of a system consisting of spray can, adapter, and a second medical device.
Figure 3C:
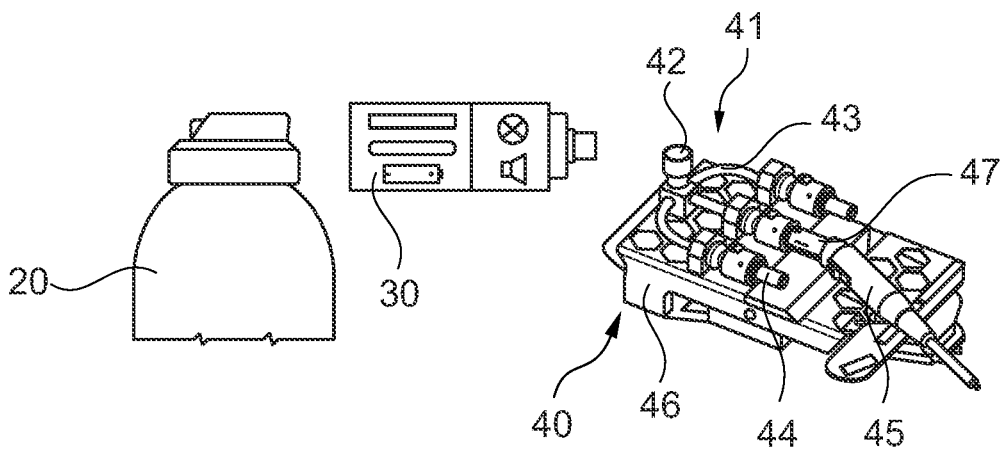
FIG. 3c a schematic representation of a system consisting of spray can, adapter, and a third medical device in the form of a distributor system with further medical devices connected thereto.

FIGS. 3a, 3b and 3c show a schematic representation of a system consisting of spray can 20, adapter 30, and a first or respectively second or respectively third medical device 40. FIGS. 3a, 3b and 3c differ only in the type of device 40 to be connected and the type of second port 8. The three elements spray can 20, adapter 30, and medical device 40 can be plugged together. This creates a continuous passage between spray can 20 and medical device 40. For example, for this purpose, the passage may be provided such that a width of the passage of the adapter 30 corresponds to a size of a passage provided by the spray head 5. Furthermore, the passage may be adapted to become bigger or smaller from the first port 7, that is, from the spray head 5, to the second port 8, that is, to the medical device 40. This may have the advantage of distributing oil in an optimized manner and avoiding oil loss.

Furthermore, the first port 7 may be configured complementary to a connection point provided on the spray head 5 of the spray can 20. This may also apply to the second port 8, which may be configured complementary to a connection point provided on the medical device 40.

When the spraying process is completed, or is to be completed, or is indicated as such by one or both of the indications 12, 13, the user removes the adapter from the spray can 20 and from the medical device 40. It may be advantageous to first remove the adapter 30 from the medical device 40 and then from the spray can 20, since different forces may be provided for force-fitting the respective ports. For example, the forces for the second port 8 in connection with the connection point provided on the medical device 40 may be configured to be smaller, for example smaller than ¾ or smaller than ½ or smaller than ¼, than the forces for the first port 7 in connection with the connection point provided on the spray head 5 of the spray can 20. This allows the spray can 20 to be handled more easily together with the adapter 30.

Furthermore, the adapter 30 is adapted to establish a smart connection with the medical device 40 to be oiled. The term smart connection means that the adapter 30 has, for example, a sensor system 48 (shown schematically) that detects whether a medical device 40 is connected, that can identify the type or, respectively, the kind of the connected medical device 40, and that can also interact with the connected medical device 40 (e.g., via a RFID chip 49 which is shown schematically), i.e., that data can be exchanged between the adapter 30 and the medical device 40.

RFID chips, which can act as readable data memory and identification features, may be a component of the sensor system. The RFID chips can be read contactlessly using near-field communication (NFC) or Bluetooth Low Energy (BLE) radio technology, for example.

Figure 4:
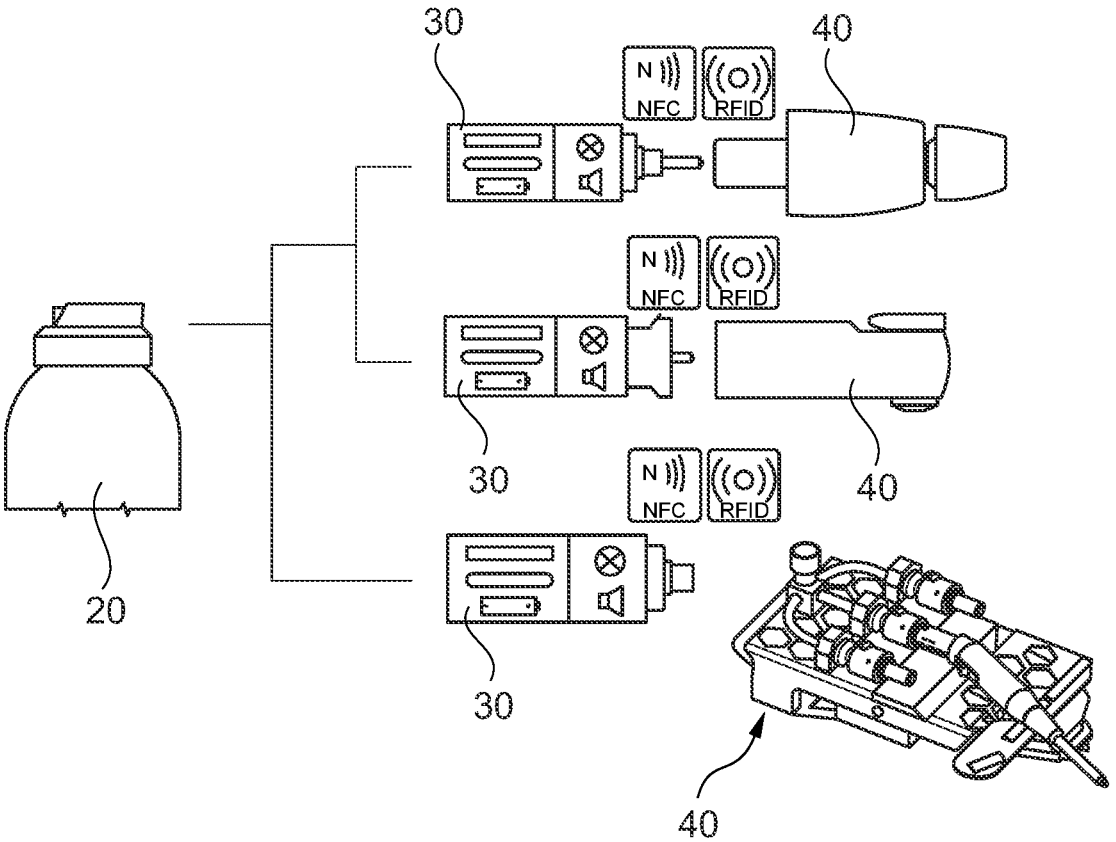
FIG. 4 is a schematic representation of a system consisting of spray can and possible adapter embodiments and corresponding port options.

FIG. 4 shows an overview of the various smart connection options of the adapter 30 to medical devices 40, summarizing the individual examples from FIGS. 3a, 3b and 3c.

In detail, the smart connection can distinguish during detection whether a medical device 40 is directly connected to the adapter 30, as shown in FIGS. 3a and 3b, or whether it is connected indirectly, as shown in FIG. 3c, via an intermediate functional unit, such as a distributor system 41. The distributor system 41 may, for example, have a port inlet 42 with a plurality of distribution passages 43 at the respective ends of which there are outlets 44. A medical instrument 45 may be connected to each of the respective outlets 44, thereby enabling an indirect connection between adapter 30 and several medical instruments 45.

The distributor system 41 may be part of a holder equipped with a sensor system of a storage tray for medical instruments 45. The storage tray is hereinafter referred to as smart tray 46. The handpieces 47 of medical instruments 45 may here also have a sensor system, for example in the form of RFID chips, so-called glass tags, specially encapsulated in a glass tube.

The sensor equipment of the individual port partners, such as adapters 30, smart trays 46 and medical devices 40 and medical instruments 45, enables smart connections between the individual port partners, which leads overall to smart networking of the port partners that are directly or indirectly connected to each other. In other words, information can be passed on, exchanged, stored and processed between the individual smart port partners.

In the specific application, data processing in the intelligent oil spray adapter 30 depends on whether a medical device 40 or a smart tray 46 to be oiled is detected and/or also identified at the second port 8 via NFC or BLE. Upon identification, the adapter 30 can read the parameters of the medical device 40 or of the smart tray 46 stored on an RFID chip and determine what amount and duration is needed to oil the corresponding device 40.

After the adapter 30 has read out the parameters of the medical device 40 or of the smart tray 46, it can, for example, output 'oiling process sufficient' via the visual indication 12 to signal that the amount of oil in the spray can 20 is sufficient for the oiling process of the respective device 40 to be oiled. If, after reading the parameters of the medical device 40 or of the smart tray 46, it is determined that the amount of oil in the spray can 20 is no longer sufficient, this may also be output via the visual indication 12 as 'oiling process insufficient'. Alternatively or also additionally, the notification as to whether there is sufficient oil in the spray can 20 may also be communicated via an acoustic signal of the acoustic indication 12 or via a color signal of the visual indication 13.

After the adapter 30 has completed the oiling process of a medical device 40 directly or indirectly via a smart tray 46 with distributor system 41, the respective parameters of the oiling process such as duration and amount of the spraying process can be stored on the respective medical device 40, in the smart tray 46 as well as in the handpiece 47 of a medical instrument 45. In other words, interaction between adapter 30 and connected parts (device 40, smart tray 46, handpieces 47 of a medical instrument 45) is possible, allowing control for an individual and precise oiling amount and spraying duration.

Furthermore, the adapter 30 as well as the smart tray 46 can not only store the respective parameters of an oiling process, but also specifically assign the respective parameters to the corresponding medical devices 40, for example via identification numbers. In other words, an interaction between adapter 30 and connected parts (device 40, smart tray 46, handpieces 47 of a medical instrument 45) is possible, which allows information such as continuous spray time and oil quantity to be stored back in the connected parts.

The data of the individual oil processes can also be read out from the oil-spray adapter 30 and the smart tray 46.

The invention relates in summary to an adapter 30 for connection to a spray can 20 dispensing a fluid such as, for example, an oil-containing aerosol. The adapter 30 is equipped with smart functions which are intended and configured to detect application parameters and preferably also state parameters of the spray can 20 and to inform the user accordingly. Application parameters are to be understood as parameters which directly or indirectly allow conclusions to be drawn about the type of current reprocessing step in a tool/instrument reprocessing. Thus, characteristic parameters can be assigned to each reprocessing step (cleaning, disinfection, sterilization, maintenance, etc.), such as reprocessing time, temperature, etc., which can be determined directly or indirectly at the adapter. It is also possible to determine the current reprocessing step on the basis of the port, etc. For example, the adapter may have a timekeeper 11 configured to perform a time measurement for a predetermined time interval, wherein the starting point of the time measurement is indicated by a start of a reprocessing step such as spraying process of the spray can 20, and an indicating element 12, 13 configured to indicate to the user to stop the spraying process upon completion of the predetermined time interval. Furthermore, the invention relates to a method for manually reprocessing a medical device 40. The optional state parameter, on the other hand, relates to a parameter that provides an indication of the state of the spray can, e.g., fill level, operability/functionality of the spray can, correct filling agent, etc.

LIST OF REFERENCE SIGNS 1 metal container
2.1 active agent solution with propellant (liquid)
2.2 propellant (gaseous)
3 rising pipe
4 valve
5 spray head
6 protection cap
7 first port
8 second port
9 power supply
10 sensor(s)
11 timekeeper
12 visual indication
13 acoustic indication
20 spray can
30 adapter
40 medical device
41 distributor system
42 port inlet
43 distributor passage
44 outlets 45 medical instrument
46 smart tray
47 handpiece
48 sensor system
49 RFID chip

The invention claimed is:

1. A reprocessing and/or maintenance system for medical instruments comprising a spray can dispensing a maintenance agent, the reprocessing and/or maintenance system comprising:
   an adapter configured to be connected to a spray can, wherein the adapter is equipped with smart functions which are provided and configured to detect application parameters of the spray can and to inform the user accordingly; and
   wherein the adapter comprises a sensor system configured to establish a smart connection with a medical device to be connected, the sensor system being configured to establish the smart connection via Near Field Communication (NFC) or a Bluetooth Low Energy (BLE) radio technology with the medical device to be connected, wherein the medical device comprises a smart tray or a medical instrument, wherein the sensor system of the adapter is configured to identify a type of the medical device by means of the smart connection and to recognize whether the medical device is connected directly or indirectly to the adapter.

2. The reprocessing and/or maintenance system according to claim 1, wherein the smart functions comprise:
   a timekeeper configured to perform a time measurement for a predetermined time interval, wherein the starting point of the time measurement is indicated by a start of a spraying process of the spray can, and
   an indicating element configured to indicate to the user to terminate the spraying process upon completion of the predetermined time interval.

3. The reprocessing and/or maintenance system according to claim 1, wherein the adapter further comprises:
   a first port configured to be connected to the spray can;
   a second port configured to be connected to the medical device; and
   a passage configured to connect the first port to the second port and to guide an aerosol dispensed by the spray can into the passage from the first port to the second port.

4. The reprocessing and/or maintenance system according to claim 1, wherein the adapter further comprises:
   a timekeeper configured to perform a time measurement for a predetermined time interval, wherein the starting point of the time measurement is indicated by a start of a spraying process of the spray can, and
   a temperature sensor configured to detect a temperature drop in a passage of the adapter, wherein the timekeeper is configured to determine the start of the spraying process based on the temperature drop.

5. The reprocessing and/or maintenance system according to claim 1, wherein the adapter comprises:
   a timekeeper configured to perform a time measurement for a predetermined time interval, wherein the starting point of the time measurement is indicated by a start of a spraying process of the spray can, and
   a pressure sensor configured to detect a pressure change in a passage of the adapter, wherein the timekeeper is configured to determine the start of the spraying process based on the pressure change.

6. The reprocessing and/or maintenance system according to claim 1, wherein the adapter further comprises:

a humidity sensor configured to detect an oil proportion of the oil-containing aerosol in a passage of the adapter; and an indicating element configured to indicate to the user to terminate a spraying process based on the oil proportion.

7. The reprocessing and/or maintenance system according to claim 1, wherein the adapter further comprises:

a position sensor configured to determine an orientation of the spray can; and an indicating element configured, based on the orientation of the spray can, to indicate to the user to terminate a spraying process.

8. The reprocessing and/or maintenance system according to claim 1, wherein the adapter further comprises: a power supply configured to supply power to operative components of the adapter.

9. The reprocessing and/or maintenance system according to claim 8, wherein the power supply comprises a replaceable battery or accumulator.

10. The reprocessing and/or maintenance system according to claim 1, further comprising:

an indicating element configured to indicate to the user to terminate a spraying process, wherein the indicating element comprises a visual or acoustic indication.

11. The reprocessing and/or maintenance system according to claim 1, wherein the adapter is configured to be connected as a reusable unit to the spray can as a one-way unit, and to a medical instrument.

12. The reprocessing and/or maintenance system according to claim 1, wherein the maintenance agent comprises an oil containing aerosol.

13. The reprocessing and/or maintenance system according to claim 1, wherein the adapter is further equipped with smart functions configured to detect also state parameters of the spray can and to inform the user accordingly.

14. The reprocessing and/or maintenance system according to claim 1, wherein the sensor system of the adapter is configured to exchange, process and store data between the adapter and the medical device by means of the smart connection, and wherein the data of the medical device are stored on an RFID chip.

15. A medical instrument reprocessing and/or maintenance system comprising:

an adapter according to claim 1, the adapter comprising:

a first port configured to connect to a dispenser;

a second port configured to connect to a medical device;

a passage fluidly connecting the first port to the second port;

one or more sensors, configured to detect a fluid passing through the passage;

one or more indicators configured to present an output signal to a user; and a processor configured to:

receive an input signal from the one or more sensors, and based on the signal, activate the one or more indicators to present the output signal to the user, the output signal representing an instruction to terminate passing of the fluid through the passage.

16. A method of manually reprocessing and/or maintaining a medical instrument, the method comprising:

providing a medical device comprising a smart tray or a medical instrument;

providing a spray can;

providing an adapter configured to be connected to the spray can, wherein the adapter is equipped with smart functions which are provided and configured to detect application parameters of the spray can and to inform a user accordingly;

establishing a smart connection between the medical device and a sensor system of the adapter, the sensor system being configured to establish the smart connection via Near Field Communication (NFC) or a Bluetooth Low Energy (BLE) radio technology, the sensor system of the adapter being configured to identify a type of the medical device by means of the smart connection and to recognize whether the medical device is connected directly or indirectly to the adapter;

connecting a first port of the adapter to the spray can;

connecting a second port of the adapter to the medical instrument;

carrying out a spraying process of the spray can for supplying mechanical components of the medical device with a reprocessing and/or maintenance agent by manual actuation of the spray can by a user;

starting a time measurement for a predetermined time interval, or a measurement of a volume flow passing through the adapter, wherein the starting point is indicated by detecting a start of the spraying process of the spray can;

indicating a completion of the predetermined time interval or the reaching of a predetermined volume flow rate, and an associated request that the spraying process be terminated.

17. The method of manually reprocessing and/or maintaining a medical instrument according to claim 16, wherein the reprocessing and/or maintenance agent comprises an oil containing aerosol.

* * * * *